(12) United States Patent
Beniash et al.

(10) Patent No.: US 12,642,891 B2
(45) Date of Patent: **\*Jun. 2, 2026**

(54) SYSTEMS AND METHODS FOR SELECTIVE COATING REMOVAL FOR RESORBABLE METAL MEDICAL DEVICES

(71) Applicant: UNIVERSITY OF PITTSBURGH—OF THE COMMONWEALTH SYSTEM OF HIGHER EDUCATION, Pittsburgh, PA (US)

(72) Inventors: Elia Beniash, Mt. Lebanon, PA (US); Avinash Jagannath Patil, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( \* ) Notice: Subject to any disclaimer, the term of this patent is extended or adjusted under 35 U.S.C. 154(b) by 735 days.

This patent is subject to a terminal disclaimer.

(21) Appl. No.: 17/205,030

(22) Filed: Mar. 18, 2021

(65) Prior Publication Data

US 2021/0205503 A1    Jul. 8, 2021

Related U.S. Application Data

(62) Division of application No. 16/073,017, filed as application No. PCT/US2017/016347 on Feb. 3, 2017, now Pat. No. 10,967,103.

(60) Provisional application No. 62/290,555, filed on Feb. 3, 2016.

(51) Int. Cl.
| | |
|---|---|
| *A61L 31/08* | (2006.01) |
| *A61L 27/04* | (2006.01) |
| *A61L 27/28* | (2006.01) |
| *A61L 27/54* | (2006.01) |
| *A61L 27/58* | (2006.01) |
| *A61L 31/02* | (2006.01) |
| *A61L 31/14* | (2006.01) |
| *A61L 31/16* | (2006.01) |
| *B05D 3/14* | (2006.01) |
| *B05D 3/06* | (2006.01) |
| *B05D 3/10* | (2006.01) |

(52) U.S. Cl.
CPC ............. *A61L 31/08* (2013.01); *A61L 27/047* (2013.01); *A61L 27/28* (2013.01); *A61L 27/54* (2013.01); *A61L 27/58* (2013.01); *A61L 31/022* (2013.01); *A61L 31/148* (2013.01); *A61L 31/16* (2013.01); *B05D 3/145* (2013.01); *A61L 2300/252* (2013.01); *A61L 2400/12* (2013.01); *A61L 2420/02* (2013.01); *A61L 2430/02* (2013.01); *B05D 3/06* (2013.01); *B05D 3/107* (2013.01)

(58) Field of Classification Search
None
See application file for complete search history.

(56) References Cited

U.S. PATENT DOCUMENTS

| | | | | | |
|---|---|---|---|---|---|
| 5,292,549 | A | \* | 3/1994 | van Ooij | ................. C23C 22/68 427/156 |
| 2005/0221072 | A1 | | 10/2005 | Dubrow et al. | |
| 2006/0171990 | A1 | \* | 8/2006 | Asgari | ................. B01J 13/0091 264/4.1 |
| 2009/0123516 | A1 | | 5/2009 | Agrawal et al. | |

FOREIGN PATENT DOCUMENTS

| | | | | | |
|---|---|---|---|---|---|
| WO | WO-2006108065 | A2 | \* | 10/2006 | ............... A61F 2/02 |
| WO | WO-2014067769 | A1 | \* | 5/2014 | ............ C08G 77/02 |
| WO | 2015069919 | A1 | | 5/2015 | |

OTHER PUBLICATIONS

Liu et al. "Biofunctionalized anti-corrosive silane coatings for magnesium alloys" 2013, Acta Biomaterialia, 9, 8671-8677 (Year: 2013).\*
Zucchi et al. "Organo-silane coatings for AZ31 magnesium alloy corrosion protection" 2008, Materials Chemistry and Physics, 110, 263-268 (Year: 2008).\*
Wankhede, R.G. et al., Development of hydrophobic non-fluorine sol-gel coatings on aluminium using long chain alkyl silane precursor, Journal of Materials Science and Engineering A, 2013, vol. 3, 224-231 (Year: 2013).\*
Liu et al., Biofunctionalized Anti-Corrosive Silane Coatings for Magnesium Alloys, Acta Biomaterialia (2013), 9:8671-8677.
Zucchi et al., Organo-Silane Coatings for AZ 31 Magnesium Alloy Corrosion Protection, Materials Chemistry and Physics (2008), 110:263-268.

\* cited by examiner

Primary Examiner — Bethany P Barham
Assistant Examiner — Paul Hoerner
(74) Attorney, Agent, or Firm — Carol A. Marmo; Eckert Seamans Cherin & Mellott, LLC

(57) ABSTRACT

The invention relates to self-assembled organosilane coatings for resorbable medical implant devices. The coatings can be prepared from coating compositions containing organosilane and can be applied to metal or metal alloy substrates. Prior to applying the coatings, the surfaces of the substrates can be pretreated. The coatings can be functionalized with a binding compound that is coupled with an active component. The coatings can be selectively removed, e.g., patterned, to expose portions of the uncoated substrate. Selecting different patterns can provide the ability to regulate or control various properties, such as, corrosion and hydrogen generation.

8 Claims, 4 Drawing Sheets

SYSTEMS AND METHODS FOR SELECTIVE COATING REMOVAL FOR RESORBABLE METAL MEDICAL DEVICES

CROSS-REFERENCE TO RELATED APPLICATIONS

This application is a divisional of U.S. Non-Provisional patent application Ser. No. 16/073,017, entitled "SYSTEMS AND METHODS FOR SELECTIVE COATING REMOVAL FOR RESORBABLE METAL MEDICAL DEVICES", filed on Jul. 26, 2018, which is a U.S. National Stage Application under 35 U.S.C. § 371 of International Application No. PCT/2017/016347, filed on Feb. 3, 2017, which claims priority under 35 U.S.C. § 119(e) from U.S. provisional patent application No. 62/290,555, filed on Feb. 3, 2016, both of which are entitled "SYSTEMS AND METHODS FOR SELECTIVE COATING REMOVAL FOR RESORBABLE METAL MEDICAL DEVICES," the contents of which are incorporated herein by reference.

GOVERNMENT SUPPORT

This invention was made with government support under Grant No. EEC0812348 awarded by the National Science Foundation (NSF). The government has certain rights in the invention.

FIELD OF THE INVENTION

The present invention relates to self-assembled organosilane-containing compositions, methods of preparing the compositions, systems and methods of depositing/applying the compositions on substrates to form coatings and selectively removing a portion of the coatings, e.g., patterning, to control or tune properties, including but not limited to, corrosion. The invention also relates to uses for the partially coated substrates as medical implant devices.

BACKGROUND OF THE INVENTION

Every year millions of orthopedic and craniofacial surgical procedures are performed in the United States, which require placement of metal, e.g., stainless steel or titanium, hardware in a patient body. After bone healing is complete, these metal implant devices are no longer needed. The devices can be left in situ or, alternatively, they can be removed. Each of these alternatives has disadvantages or problems associated therewith. For example, leaving the hardware in situ increases the chances of infection and rejection, and removal of the hardware requires a second surgery and causes a risk of infection, pain and discomfort to the patient, as well as it being an additional expense. To overcome these disadvantages or problems, there has been developed a number of resorbable polymeric devices that are effective to degrade over a period of time. Thus, the device does not remain in-situ and there is no need to surgically remove the device because when the device is no longer needed, the polymeric material degrades or dissolves within the patient body. However, there are also disadvantages associated with the resorbable polymer devices. For instance, it has been found that the resorbable polymeric materials, which are used for the construction of biodegradable medical implant devices, can lack mechanical strength as compared to that exhibited by metal implants and have a limited set of applications. As a result, there is an interest in the art to identify materials that degrade over time while demonstrating sufficient mechanical strength prior to degradation.

It has been found that the development of new technologies for implantable devices based on resorbable magnesium and magnesium alloys has the potential to make a significant clinical impact. Magnesium and magnesium alloys are suitable materials for the construction of resorbable devices because they have mechanical properties compatible to bone and can be resorbed over a period of time. However, there are other properties of magnesium and magnesium alloys that are problematic for their use as medical implant devices. For example, magnesium is not typically used in the fabrication of medical implant devices primarily because the corrosion of magnesium results in the production of hydrogen. Medical implant devices constructed of magnesium can cause the accumulation of hydrogen in areas surrounding the device and thus, result in the formation of gas cavities in the patient body. In order for magnesium and magnesium alloys to be considered as suitable materials for use in constructing medical implant devices, the rate of corrosion of these materials needs to be closely monitored and controlled to prevent formation of gas cavities. Thus, there are a number of important characteristics that have to be controlled in order to achieve the best clinical outcomes including, for example, rate of resorption, control of corrosion products, tissue integration and osteoconduction properties of the device.

It is known to deposit a coating composition on the surface of metal implant devices to modify the properties, e.g., corrosion, of the devices. Coatings for metal-based implants have been classified as conversion or deposition coatings. Conversion coatings are generally formed in situ through a reaction between the substrate and its environment, and are typically inorganic. For application to magnesium or magnesium alloys, these coatings are often composed of oxides, phosphates or fluorides. Conversion coatings typically advantageously exhibit good adhesion to the substrate, however, there are disadvantages associated with mechanical durability and biocompatibility of these coatings. Deposition coatings are typically organic or ceramic and are applied through physical interactions with the surface of a metal substrate. For application to magnesium or magnesium alloy substrates, deposition coatings often require a conversion coating pre-treatment to improve adhesion to the alloy substrates. In the absence of a conversion coating pre-treatment, e.g., one-step coatings, it is likely that the coated substrate will demonstrate poor adhesion and corrosion protection.

There is a desire in the art to develop a mechanism for controlling the rates of corrosion of magnesium and magnesium alloy in order to reduce or minimize the production and accumulation of hydrogen resulting therefrom, and to construct medical implant devices from materials that demonstrate sufficient mechanical strength when needed and degradation over time when no longer needed. Further, there is a desire to develop a coating that is effective to control rates of corrosion of magnesium and magnesium alloy and to reduce or minimize the production and accumulation of hydrogen resulting therefrom, and demonstrates good adherence or adhesion to the magnesium and magnesium alloy. Moreover, it would be advantageous for the coatings to be capable of being customized or modified to allow properties, such as, corrosion and hydrogen generation, to be tuned or regulated.

SUMMARY OF THE INVENTION

An object of the present invention is to develop novel coating compositions for application to magnesium and magnesium alloy substrates for use as medical implant devices. In particular, an object of the present invention is to develop hybrid bio-inspired anticorrosive coatings based on self-assembled multilayer organosilane. The surface of these coatings can be modified via covalent bonding with an active component, including bioactive molecules, such as proteins and peptides. These surface chemistry modifications can provide the ability to control different physical chemical properties of the coatings, including but not limited to, hydrophobicity and charge, as well as bioactivity. These coatings can effectively control the degradation rate of magnesium and magnesium alloy resorbable devices to insure safety and efficiency, and to induce desirable tissue responses. Further, these coatings can be functionalized to regulate the rate of corrosion and insure the device integration into target tissues. Furthermore, these coatings can be selectively removed, e.g., patterned, to expose portions of uncoated substrate, which can be effective to regulate pre-selected properties, such as, but not limited to corrosion rate.

In one aspect, the invention provides a medical implant device including a magnesium or magnesium alloy substrate, having a first surface and an opposing second surface; a self-assembled organosilane-containing coating applied to at least one of the first and second surface; and a pattern applied to the coating on at least one of the first and second surfaces. The pattern includes one or more areas of selective removal of the coating from the substrate. Further, a binding compound can be combined with the coating and furthermore, an active component can be coupled to the binding compound.

In certain embodiments, a binding compound is combined with the coating. Furthermore, an active component can be coupled to the binding compound.

The device can also include a pretreatment applied to the at least one of the first and second surfaces, and the coating applied to the pretreatment.

In certain embodiments, a first portion of the pattern has a first configuration and a second portion of the pattern has a different, second configuration.

The one or more areas of selective removal of the coating is effective to increase the corrosion rate of the substrate.

In another aspect, the invention provides a method of forming a patterned coating on a medical implant device. The method includes obtaining an uncoated substrate having a top surface and an opposing bottom surface; preparing a coating composition including organosilane; applying the coating composition to at least one of the top and bottom surfaces of the uncoated substrate to form a coating thereon; and selectively removing a portion of the coating to expose the uncoated substrate.

The method can further include functionalizing the coating with a binding compound, and coupling an active component to the binding compound.

The step of selectively removing can include a process selected from the group consisting of laser ablation, ion etching, electron beam etching and combinations thereof. The selective removal of a portion of the coating forms a pattern exposing one or more areas of the uncoated substrate. Furthermore, one or more of the size, density and spatial distribution of the one or more areas of the uncoated substrate is controlled to regulate a pre-selected property, such as, corrosion rate.

In certain embodiments, a portion of the coating is selectively removed to expose the uncoated substrate on both of the top and bottom surfaces.

DETAILED DESCRIPTION OF THE INVENTION

Figure 1:
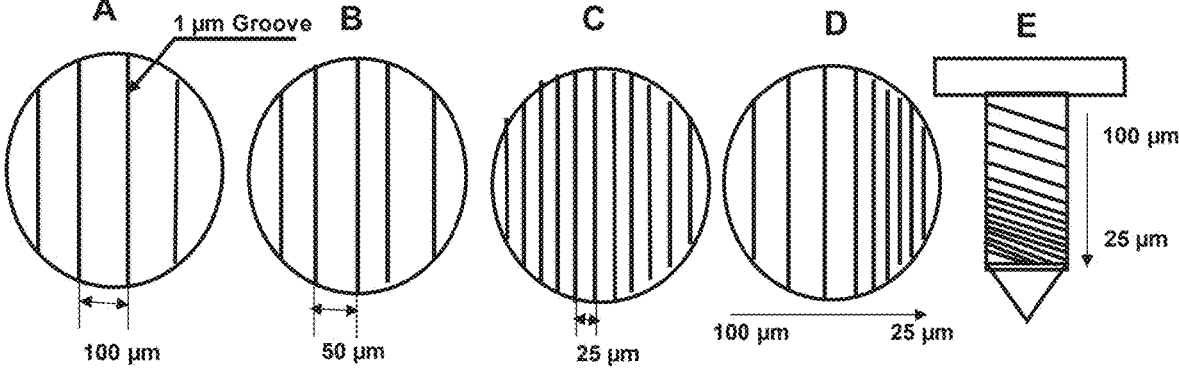
FIG. 1 is a schematic that shows various patterns formed by selectively removing a coating deposited on a magnesium or magnesium alloy substrate to expose portions of uncoated substrate for use in regulating corrosion rate, in accordance with certain embodiments of the invention.

The invention generally relates to self-assembled organosilane-containing coating compositions applied to, or deposited on, substrates to form patterned coatings; and methods of applying/depositing the coating compositions onto the substrates, and subsequently selectively removing a portion or part of the coatings to expose the uncoated substrates (e.g., underneath the coatings). The invention also relates to the use of the patterned coated substrates in constructing and fabricating medical implant devices for use in various surgical applications, such as, but not limited to, dental, orthopedic, craniofacial, and cardiovascular.

The substrates, e.g., medical implant devices, can be composed of a wide variety of materials that are known in the art for such purposes. In accordance with the objectives of controlling the rates of corrosion of the substrates in order to reduce or minimize the production and accumulation of hydrogen resulting therefrom, and to construct medical implant devices from materials that demonstrate sufficient mechanical strength when needed and degradation over time when no longer needed, it is preferred that the substrates, e.g., medical implant devices, be composed of magnesium or magnesium alloy.

In certain embodiments, the coating composition is directly applied to, or deposited on, the surface of the substrate, e.g., medical implant device, in the absence of any pretreatment or pre-coating of the surface, to form a coating thereon. However, in other embodiments, for the purpose of improving the adherence and/or adhesion of the coating to the surface of the substrate, a pretreatment or pre-coating is applied to the surface of the substrate prior to applying the coating composition. Suitable pretreatments or pre-coatings include those known in the art for use with magnesium or magnesium alloy substrates to improve adherence and/or adhesion of a coating to the surface of the substrates.

Following the application of the coating composition and formation of the resultant coating on the surface of the substrate, the coating is partially removed. The partial removal of the coating from the surface of the substrates can be selectively conducted by forming various patterns of coated and uncoated substrate. In certain areas of the pattern, the uncoated surface of the substrate is exposed and in other areas, the surface has the coating applied thereto. The selective removal, e.g., pattern, can be effective to regulate or control certain properties of the substrate, such as, corrosion rate and hydrogen generation.

Without intending to be bound by any particular theory, it is believed that the patterned coatings are effective to modify various properties and characteristics of the underlying magnesium/magnesium-containing substrate of the a medical implant device. For example, a patterned coating can be effective to control one or more of the following properties of the magnesium/magnesium-containing substrate: corrosion rate, production/accumulation of hydrogen, rate of resorption, tissue integration and osteoconduction. In certain embodiments, the patterned coating can be effective to reduce or preclude the corrosion rate and, in turn, the production/accumulation of hydrogen. Further, the surface of the coated portions of the substrate can include covalent bonding with different molecules, including bioactive molecules, such as proteins and peptides.

Surface chemistry modifications can provide the ability to control different physical chemical properties of the coating, including but not limited to, hydrophobicity and charge, as well as bioactivity. Furthermore, the patterned, substrate surface including coated and uncoated portions or parts can be used to control or regulate pre-selected or desired properties.

Conventional apparatus and techniques are generally known for preparing and applying/depositing a silane coating composition onto a substrate, modifying or functionalizing the surface of the formed silane coating, and selectively removing a portion of the coating formed. For example, various amphiphilic organosilanes are used to form nanostructured films for glass coating applications, and the application of organosilanes for corrosion control are known. However, there is a need in the art to develop organosilane-containing compositions for use in coating resorbable metallic, e.g., magnesium and magnesium alloy, substrates, such as medical implant devices. In particular, the coatings for medical implant devices require special properties, including the ability to adapt to the intrinsically unstable physical and chemical environment of a corroding metal substrate, as well as the ability to be functionalized with bioactive molecules.

In general, self-assembled coatings, e.g., monolayers, are thin films produced by deposition of materials, such as, organosilanes. The coatings are formed, e.g., spontaneously, on a surface of a substrate by adsorption and include a head group, tail and functional end groups. The head group can be in a vapor phase or a liquid phase. The head group assembles onto the substrate surface, while the tail group organizes and assembles farther from the surface of the substrate. The substrate and head group are selected to react with each other. In certain embodiments, a hydrophilic end (e.g., head group) may bond with the substrate surface while a hydrophobic end may be opposite the hydrophilic end.

In accordance with the invention, the self-assembled coating compositions include organosilane, such as, hybrid organosilanes. In certain embodiments, the coating compositions include amphiphilic organosilanes having an aliphatic tail containing a backbone of 4 to 20 carbon atoms (i.e., $C_4$ to $C_{20}$) and a silane head. A non-limiting example of suitable organosilanes include alkylsilanes, such as, alkyltrialkoxysilanes including, but not limited to, decyltriethoxysilane. In certain embodiments, the alkyltrialkoxysilanes, such as, but not limited to, decyltriethoxysilane, are co-polymerized with another polymer component, such as, but not limited to, tetramethoxysilane (TMOS). Further, in certain embodiments, the alkyltrialkoxysilanes are combined with a crosslinking material, such as, but not limited to, a UV crosslinking agent.

The self-assembled coating compositions are applied or deposited onto the magnesium or magnesium alloy surface, e.g., of the medical implant device. The magnesium alloy may be selected from a wide variety of magnesium alloys known in the art for constructing medical implant devices. Non limiting examples of suitable magnesium alloys include those magnesium-containing compositions described in PCT Application having International Application No. PCT/US2012/058939 entitled "Biodegradable Metal Alloys" filed on Oct. 5, 2012, published as US20140248288 on Sep. 4, 2014, and issued as U.S. Pat. No. 9,510,932 on Dec. 6, 2016, and based on U.S. Provisional Patent Application 61/544,127 entitled "Biodegradable Metal Alloys" filed on Oct. 6, 2011, which are incorporated in their entirety herein by reference.

In certain embodiments, the magnesium alloys include elemental magnesium and one or more other elemental components, such as, but not limited to, iron, zirconium, manganese, calcium, yttrium and zinc. The amount of each of the components can vary and, in general, the amounts are selected such that the resulting magnesium alloys are within acceptable non-toxic limits, sufficiently biocompatible and degradable over a period of time.

In general, the self-assembled organosilane coatings can be formed using known apparatus and conventional coating techniques, including, but not limited to, physical vapor deposition, electro-deposition or electro-less deposition. For example, a self-assembled coating can be formed on a magnesium or magnesium alloy substrate at ambient conditions by spinning, dipping or spraying techniques, which are known in the art. In certain embodiments, a coating is formed by employing a deep-coating process at ambient conditions. This process includes combining organosilane and solvent, e.g., water, to form a solution and applying the solution to a magnesium or magnesium alloy substrate by dipping/immersing the substrate into a bath of the solution. The immersion can be for a time period ranging from minutes to hours and, typically includes sufficient time to allow the organosilane to bond to the substrate. As previously described, the solution can be applied directly to the substrate (in the absence of pretreating or pre-coating) or the solution can be applied to a pretreated or pre-coated substrate. Subsequent evaporation of the solvent, by conventional methods, induces the organosilane to self-assemble into micro- or nano-structures and thin film. The resulting coating, e.g., thin film, is rigid, uniform and has a thickness that can vary from about 100 nanometers to tens of micrometers The coating thickness can depend on various factors including the organosilane composition components, the process conditions and the intended use of the coated substrate. In one embodiment, the coating has a thickness of about 1 μm. Further, the coating, e.g., laminar structure, can include multiple layers. In certain embodiments, the coating may be composed of about 30 nm thick layers. Furthermore, the coating can be hydrophobic which may be particularly beneficial for cardiovascular applications.

The coating process in accordance with the invention can optionally include pre-treating or pre-coating the surface of the substrate prior to applying/depositing the organosilane coating composition thereto. The pre-treatment or pre-coating is applied to, or deposited on, the bare, e.g., uncoated, surface of the magnesium or magnesium alloy substrate. The pre-treatment/pre-coating step can vary and may be selected from known pretreatment compounds/compositions, techniques and processes that are employed to improve adherence or adhesion of a coating to the surface of a substrate. In certain embodiments, the pretreatment includes polishing and/or etching the uncoated substrate with nitric acid, and/or passivating with sodium hydroxide. Without intending to be bound by any particular theory, it is believed that pretreating the substrate prior to applying the coating composition, e.g., solution, results in a more uniform coating having improved adhesion or adherence properties, as compared to coatings that are formed in the absence of pretreating the substrate.

The coating in accordance with the invention has numerous advantages as compared to conventional coatings, including, but not limited to, for example, tunability and controllability. The thickness of the coating and its mechanical properties can be tuned or controlled. For example, using organosilanes with UV crosslinkable groups provides the ability to increase stiffness simply by exposure to a UV source. Further, copolymerizing organosilanes with tetramethoxysilane produces liquid-like coatings having increased flexibility, which may be particularly useful for cardiovascular applications.

Furthermore, the surface of the coatings can be modified or functionalized to attach or bind an active component. A binding compound, such as, but not limited to amine, carboxyl, thiol, hydroxyl and mixtures thereof, is used to bind one or more active components to the coatings. In certain embodiments, the binding compound is attached to the surface of the coating. For example, a plurality of molecules containing silane groups, e.g., aminosilanes, such as, but not limited to aminopropyl-trimethoxysilane, can be covalently attached to the surface of the coating to provide chemistry for attachment of the active component, such as, but not limited to alkaline phosphatase, or for modifying hydrophobicity of the surface. In certain other embodiments, the binding compound can be permeated or encapsulated within the composition that is applied to the substrate to form the coating.

As used herein, the term "active component" and related terms refer to at least one molecule, compound, complex, adduct and/or composite that exhibits one or more beneficial activities, such as, therapeutic activity, diagnostic activity, biocompatibility, corrosion-resistance, and the like. Active components that exhibit a therapeutic activity can include bioactive agents, pharmaceutically active agents, drugs and the like. Non-limiting examples of bioactive agents include, but are not limited to, bone growth promoting agents, such as growth factors, drugs, proteins, antibiotics, antibodies, ligands, DNA, RNA, peptides, enzymes, vitamins, cells and the like, and combinations thereof.

With the binding of one or more active components, the coatings and coated magnesium or magnesium alloy substrates, can be effective to combine anti-corrosion properties with bioactive surface modifications, which can facilitate improved tissue integration and induce desired biological responses in resulting medical implant devices.

Moreover, the coatings, e.g., thin films, formed as a result of the self-assembled coating compositions applied or deposited onto the magnesium or magnesium alloy surface, e.g., of the medical implant device, can be partially, e.g., selectively, removed to regulate or control various properties, such as, corrosion. The selective removal of the coating to expose portions or parts underneath, e.g., uncoated substrate, can be performed by employing various conventional techniques and apparatus known in the art. For example, selective removal of a coating can be conducted using one or more of laser ablation, ion etching and electron beam etching. In certain embodiments, the selective removal can include forming various patterns in the coating. The patterns can include a plurality of lines or grooves. The number, width and configuration of the lines or grooves can vary, and may correspond to, or depend on, a pre-determined amount of exposed uncoated surface necessary to achieve preselected or desired properties. Further, the pattern can be formed on one or more surfaces of the substrate. For example, wherein the substrate has upper and lower surfaces, the pattern can be formed on one or both of these surfaces.

Without intending to be bound by any particular theory, it is believed that selective removal of the coating eliminates inhibition of the corrosion in the exposed areas of the substrate and increases the rate of corrosion. By changing size, density and spatial distribution of exposed areas of the substrate, the corrosion rate of the entire substrate, e.g., medical implant device, or portions or parts thereof can be controlled or tuned.

FIG. 1 is a schematic showing a plurality of coated substrates A, B, C, D and E, having a given surface area and various removal patterns formed by lines, e.g., grooves, applied to the surface. As shown in FIG. 1, substrate B has a greater density of grooves, e.g., a higher number of grooves or less spacing between the grooves, in the pattern as compared to substrate A. Substrate C has a greater density of grooves in the pattern as compared to both substrates A and B. In substrate A, there are four, 1-um wide grooves spaced apart by a distance of 100 um. Substrate B has five grooves and shows a spacing of 50 um, and substrate C has 11 grooves with a spacing of 25 um. An increase in the density, e.g., higher number of grooves or less spacing between the grooves, results in an increase in the exposed area of the uncoated substrate and therefore, an increase in the rate of corrosion. A similar effect may be achieved by varying the width of the exposed areas, e.g., grooves, without changing their density. In FIG. 1, substrates D and E show that the rate of corrosion can be spatially regulated in different portions or parts, e.g., of a medical implant device, by having the density of the grooves be different for certain portions or parts. That is, the pattern for substrate D has a lesser density of grooves on the left-side portion of the disk and a greater density of grooves toward the right side portion of the disk. From left to right, the spacing is shown to decrease from 100 um to 25 um. Similarly, the pattern for the screw E has a lesser density of grooves at the top portion of the shaft and a greater density of grooves toward the lower portion of the shaft. From top to bottom, the spacing is shown to decrease from 100 um to 25 um.

Patterned, organosilane-coated, magnesium or magnesium-containing substrates, in accordance with the invention, are generally effective for tissue regeneration and, in particular, bone regeneration, within a body of a patient. These substrates can be employed as materials of construction for various medical implant devices. Non-limiting examples of suitable medical devices include, but are not limited to, scaffolds, plates, meshes, staples, screws, pins, tacks, rods, suture anchors, tubular mesh, coils, x-ray markers, catheters, endoprostheses, pipes, shields, bolts, clips or plugs, dental implants or devices, such as but not limited to occlusive barrier membranes, graft devices, bone-fracture healing devices, bone replacement devices, join replacement devices, tissue regeneration devices, cardiovascular stents, nerve guides, surgical implants and wires.

It will be appreciated by those skilled in the art that changes can be made to the embodiments described above without departing from the broad inventive concept thereof.

It is understood, therefore, that this invention is not limited to the particular embodiments disclosed and the following examples conducted, but it is intended to cover modifications that are within the spirit and scope of the invention.

EXAMPLES

Example 1—Patterning of Coated Mg Samples

Figure 2:
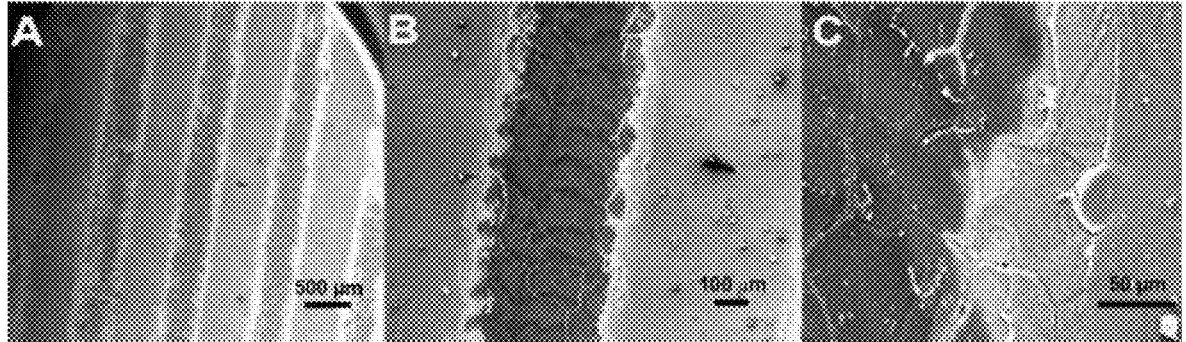
FIG. 2 shows SEM micrographs A, B and C of laser ablated substrate samples at various magnifications, i.e., A is low magnification, B is intermediate magnification and C is high magnification, wherein the coating is completely removed in the ablated areas and the underlying metal remains intact, in accordance with certain embodiments of the invention.

A plurality of Mg—OH-AS (wherein AS represents alkylsilane) coated substrate samples were patterned with the use of laser ablation. Several 0.2 mm-wide lines were etched on each of the top and bottom surfaces of AS-coated disks by laser ablation (as shown in views A, B and C of FIG. 2). The laser ablation was conducted using a low energy setting such that the treatment removed only the AS coating and the underlying substrate remained intact.

Example 2—Hydrogen Evolution

Figure 3:
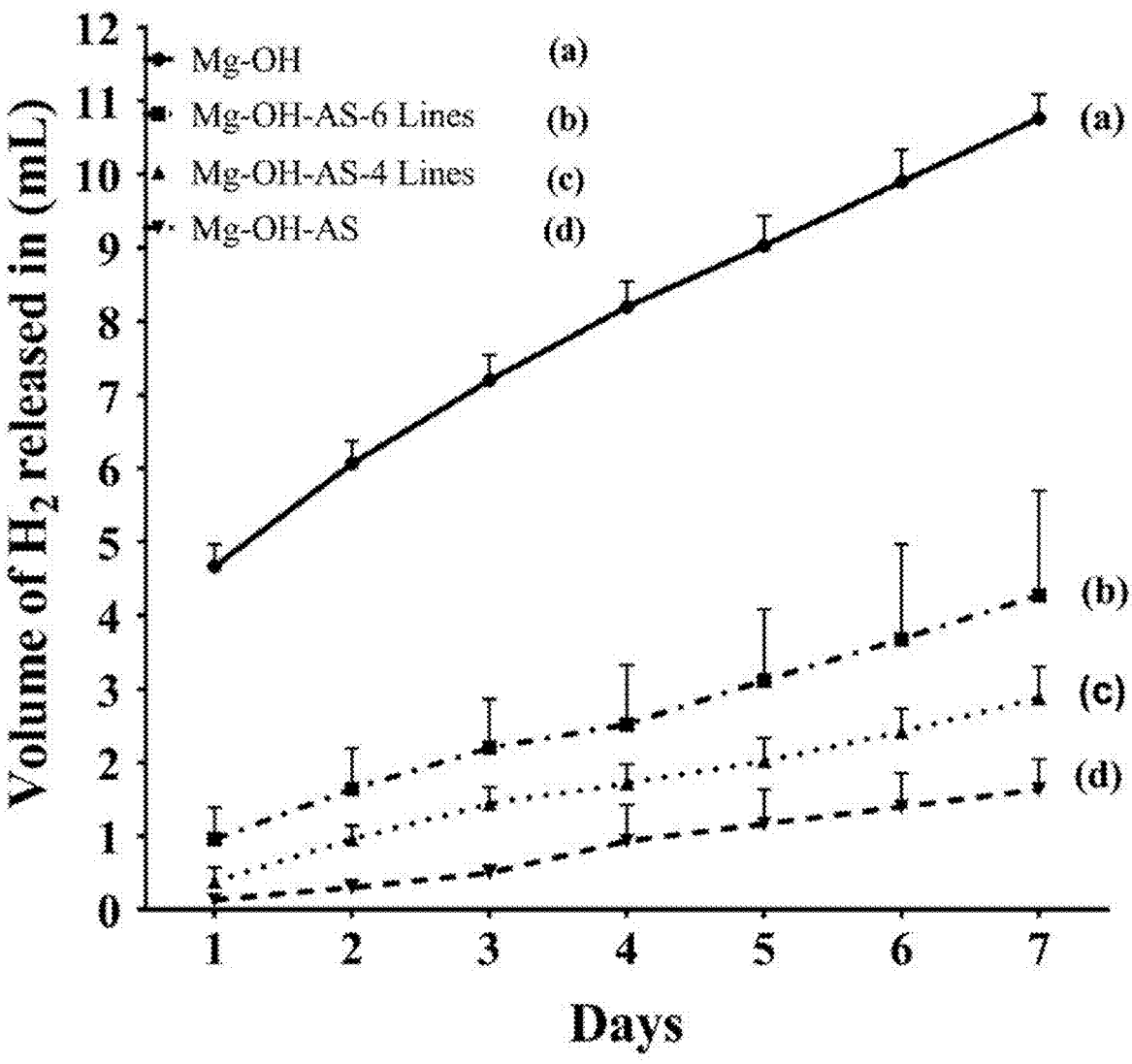
FIG. 3 is a plot of hydrogen evolution verses time (i.e., days) for patterned Mg—OH-AS coated substrate samples, in accordance with certain embodiments of the invention.

Four experimental groups of three samples each were assembled, including: (a) bare Mg—OH disks (absent of a coating), (b) Mg—OH-AS coated disks with 6-line patterns, (c) Mg—OH-AS coated disks with 4-line patterns, and (d) fully-coated Mg—OH-AS disks (absent of a pattern). Hydrogen evolution experiments were conducted over a seven-day period. As shown in FIG. 3, the results of these experiments demonstrated that the presence of patterning increased the corrosion rate of the Mg—OH-AS samples (i.e., (b) and (c)) as compared to the Mg—OH-AS sample absent of patterning (i.e., (d)). However, the rate of corrosion was significantly lower for the patterned substrates (i.e., (b) and (c)) as compared to the bare Mg—OH substrate (i.e., (a)). The differences among the four groups were highly statistically significant ($p < 0.0001$). Furthermore, the initial corrosion burst was prevented in the patterned Mg—OH-AS samples (i.e., (b) and (c)). These results demonstrate that the corrosion rate of the substrate, e.g., medical implant device, can be fine-tuned by partial removal of the coating from the substrate.

Example 3—Prevention of Calcium Phosphate Deposition

It was determined that local pH increase in an area around the corroding Mg devices led to spontaneous calcium phosphate precipitation. This is a highly undesirable outcome, especially in cardiovascular applications (e.g., stents and other devices). The present data indicated that the AS coatings effectively prevented calcium phosphate precipitation and therefore, may be effective to reduce calcium phosphate formation in the area of a medical implant device constructed of the substrate in accordance with the invention.

Example 4—Elemental Analysis

Figure 4:
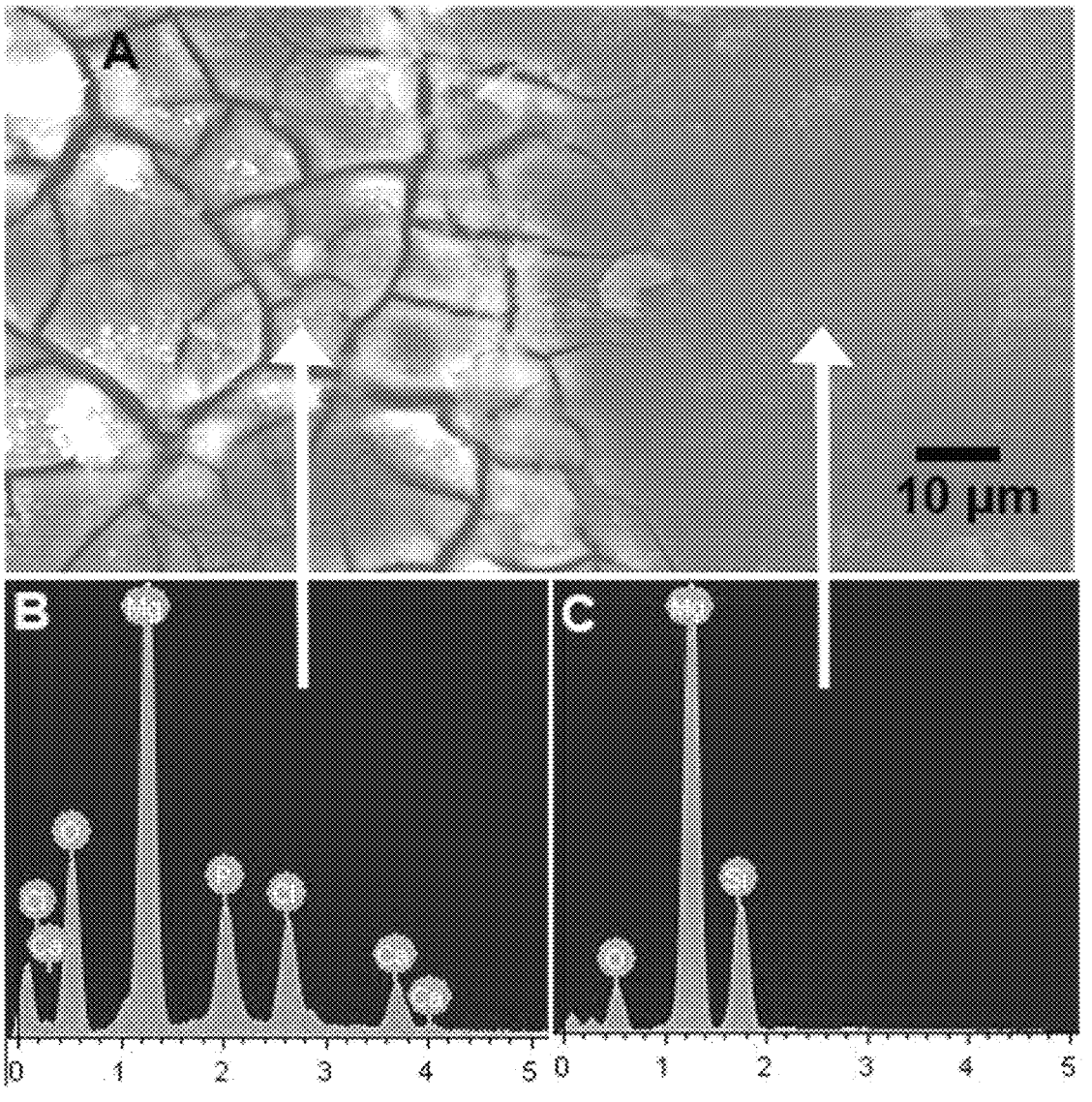
FIG. 4 is a SEM micrograph that shows a patterned magnesium disk exposed to simulated body fluid (SBF) for a period of seven days with a bare Mg side on the left and AS coated on the right, and wherein insets show an EDS spectra from the respective areas, in accordance with certain embodiments of the invention.

Elemental analysis of the patterned Mg samples containing AS coated and non-coated areas was conducted and revealed the presence of calcium and phosphate on exposed areas while these elements were not detected on the coated areas (see FIG. 4). The results of the elemental composition are shown in Table 1 below.

TABLE 1

| | The elemental composition of the AS coated and uncoated areas of a Mg sample | | | |
|---|---|---|---|---|
| Element | Corroded Area | | Coated Area | |
| K edge | Weight % | Atomic % | Weight % | Atomic % |
| O | 48.79 | 62.24 | 25.81 | 35.57 |
| Mg | 29.69 | 24.93 | 50.88 | 46.14 |
| P | 8.76 | 5.77 | — | — |
| Cl | 8.57 | 4.93 | — | — |
| Ca | 4.19 | 2.13 | — | — |
| Si | — | — | 23.31 | 18.30 |

We claim:

1. A medical implant device, comprising:
a substrate composed of a material selected from the group consisting of magnesium and magnesium alloy having an outer surface;
a thin film, self-assembled coating applied to the outer surface of the substrate, the self-assembled coating comprising:
a laminar structure;
a plurality of layers;
a hybrid amphiphilic alkylsilane consisting of a hydrophobic aliphatic tail with a $C_4$ to $C_{20}$ aliphatic backbone and a hydrophilic silane head reactive with the substrate; and
a cross-linking agent combined with the alkylsilane,
wherein the coating has a thickness of about 1 um;
an aminosilane binding compound attached to the surface of the self-assembled coating; and
an active component coupled to the aminosilane binding compound,
wherein the self-assembled coating reduces degradation rate of the substrate.

2. The device of claim 1, further comprising pretreatment applied to the outer surface of the substrate and the coating being applied to the pretreatment.

3. The device of claim 1, wherein the coating comprises a co-polymer of decyltriethoxysilane and tetramethoxysilane.

4. The device of claim 1, wherein the binding compound comprises 3-aminopropyl-trimethoxysilane.

5. The device of claim 1, wherein said device is a cardiovascular medical implant device.

6. The medical implant device of claim 1, wherein the multilayer laminar structure comprises layers having a thickness of about 30 nm.

7. The medical implant device of claim 1, wherein the self-assembled coating comprises a pattern having selective removal of the coating to expose an uncoated substrate.

8. The medical implant device of claim 1, wherein the plurality of layers comprises a plurality of 30 nm-thick layers.

* * * * *